United States Patent

Mollenkopf et al.

Patent Number: 5,710,330
Date of Patent: Jan. 20, 1998

[54] PROCESS FOR PREPARING ALKANEPHOSPHONIC ANHYDRIDES

[75] Inventors: Carl Christoph Mollenkopf, Frankfurt am Main; Ernst Ingo Leupold, Neu-Anspach; Günter Roscher, Kelkheim, all of Germany

[73] Assignee: Hoechst AG, Frankfurt, Germany

[21] Appl. No.: 556,859

[22] Filed: Nov. 2, 1995

[30] Foreign Application Priority Data

Nov. 4, 1994 [DE] Germany ............ 44 39 362.8

[51] Int. Cl.⁶ .................................. C07F 9/38
[52] U.S. Cl. .................................. 562/878
[58] Field of Search ........................ 562/878

[56] References Cited

U.S. PATENT DOCUMENTS

| | | |
|---|---|---|
| 2,268,157 | 12/1941 | Marvel . |
| 2,727,067 | 12/1955 | Craig et al. . |
| 3,454,683 | 7/1969 | Kampe et al. . |
| 3,689,548 | 9/1972 | Maier . |
| 4,195,035 | 3/1980 | Kleiner et al. . |
| 4,267,125 | 5/1981 | Dürsch et al. . |

FOREIGN PATENT DOCUMENTS

| | | |
|---|---|---|
| 0015483 | 4/1982 | European Pat. Off. . |
| 15483 | 4/1982 | European Pat. Off. . |
| 2758580 | 7/1979 | Germany . |
| 2811628 | 9/1979 | Germany . |
| 2225545 | 2/1982 | Germany . |

OTHER PUBLICATIONS

Grant, D., et al, *J. Polymer Sci.:Part A–1* 5:57–75 (1967).

*Primary Examiner*—C. Warren Ivy
*Assistant Examiner*—Jean F. Vollano
*Attorney, Agent, or Firm*—Connolly & Hutz

[57] ABSTRACT

Process for preparing alkanephosphonic anhydrides of the formula (I)

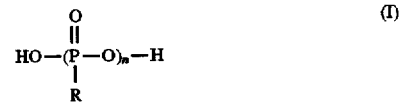

where R is straight-chain or branched unsubstituted $C_1$–$C_6$-alkyl and $n \geq 3$, which comprises pyrolytically eliminating water from an alkanephosphonic acid of the formula (II) or a pyroalkanephosphonic acid of the formula (III)

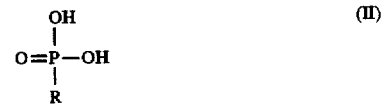

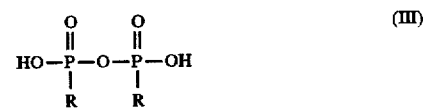

where R is straight-chain or branched $C_1$–$C_6$-alkyl, without addition of solvent and removing the water from the reaction mixture by means of an inert gas stream.

20 Claims, No Drawings

PROCESS FOR PREPARING ALKANEPHOSPHONIC ANHYDRIDES

The present invention relates to a process for preparing alkanephosphonic anhydrides directly from the corresponding acids with elimination of water, without condensation agents having to be used and without an intermediate, for example the corresponding alkanephosphonic dichlorides, being necessary for this purpose.

Various methods are known for preparing alkanephosphonic anhydrides. These generally start from the corresponding alkanephosphonic acids. These can be converted into the alkanephosphonic dichlorides using, for example, phosphorus trichloride, thionyl chloride or phosgene (DE-A 2225545). The alkanephosphonic anhydrides can then be obtained from the alkanephosphonic dichlorides by different synthetic routes:

The alkanephosphonic dichloride can be reacted either with alkanephosphonic acid or the stoichiometric amount of water to give the alkanephosphonic anhydride (EP 154 83), with hydrogen chloride being simultaneously formed. Another known method is the trans-anhydridation of alkanephosphonic acid with, for example, acetic anhydride (DE-A 2758580). In this process, a mixture of alkanephosphonic acid and acetic anhydride is heated to reflux and the acetic acid formed is continually distilled off. A further process comprises the reaction of alkanephosphonic dichloride with the stoichiometric amount of dimethyl alkanephosphonate, with chloromethane being simultaneously formed (D. Grant, J. R. Van Wazer, C. H. Dungan, J. Polym. Science, A-15, 1967, 57). The direct condensation reaction of the alkanephosphonic acid by simple pyrolysis is described in DE-A 2811628. In contrast to this reference, D. Grant, J. R. Van Wazer, C. H. Dungan (J. Polym. Science A-15, 1967, 57) describe the thermal elimination of water from, for example, methane phosphonic acid by simple thermolysis as not able to be carried out.

The comparative example shows, in agreement with the work of D. Grant, J. R. Van Wazer, C. H. Dungan (J. Polym. Science A-15, 1967, 57), that a pyrolysis in which the condensation product water is not prevented from backreacting with anhydride already formed leads only to a very unsatisfactory anhydride content. The procedure proposed in DE-A 2811628 therefore does not represent, as also already shown in DE-A-4 126 235, an economical process for preparing the alkanephosphonic anhydrides. On the other hand, however, the use of alkanephosphonic dichlorides results in the formation of large amounts of toxic or corrosive gases. In addition, large amounts of water-withdrawing auxiliaries, for example acetic anhydride or dicyclohexylcarbodiimide (DCC), have to be used in the condensation.

It is therefore an object of the invention to develop a process which gives alkanephosphonic anhydrides in high yield and purity, without the formation of toxic or corrosive gases, i.e. circumventing the corresponding alkanephosphonic dichlorides as intermediate, and also avoiding condensation agents. In addition, a way has to be found of preventing water formed in a thermal condensation of the alkanephosphonic acid from backreacting with the alkanephosphonic anhydride already formed.

This object is achieved by a process for preparing alkanephosphonic anhydrides of the formula (I)

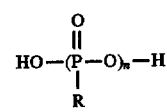

where R is straight-chain or branched unsubstituted $C_1$–$C_6$-alkyl and $n \geq 3$, which comprises pyrolytically eliminating water from an alkanephosphonic acid of the formula (II) or a pyroalkanephosphonic acid of the formula (III)

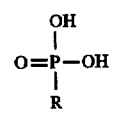

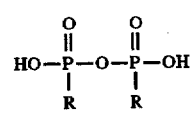

where R is straight-chain or branched $C_1$–$C_6$-alkyl, without addition of solvent and removing the water from the reaction mixture by means of an inert gas stream.

The process can be advantageously used for preparing methanephosphonic, ethanephosphonic and propanephosphonic anhydrides; n is here at least 3, generally between 3 and 150, in particular 5 and 100.

The advantages of this process are based on the water formed in the thermal condensation being able to be completely removed from the equilibrium by means of the inert gas stream and the backreaction thus being prevented. It was surprising that a simple technical measure such as passing through an inert gas stream significantly increases the yield and purity of the anhydrides (see Example 1/comparative example). Furthermore, the process of the invention allows significantly lower temperatures, giving the advantages of reduced corrosion and a reduced energy consumption. Furthermore, the products contain significantly lower amounts of decomposition products which cause turbidity. Moreover, auxiliaries such as water-withdrawing agents (DCC, acetic anhydride) can be omitted. In addition, circumventing the alkanephosphonic dichloride as starting material enables the formation of corrosive and toxic gases in the synthesis of the anhydride to be avoided.

To carry out the process, the alkanephosphonic acid or pyroalkanephosphonic acid is heated to from 200° to 350° C., preferably from 250° to 300° C., in an inert atmosphere. On reaching 200° C., the reaction vessel is evacuated and at the same time an inert gas stream is passed through the melt, so that a vacuum of from 2 to 10 mbar, preferably from 3 to 4 mbar, is achieved.

The temperature is selected so that, in the vacuum selected, it lies from 30° to 70° C., preferably from 40° to 60° C., below the corresponding boiling or sublimation point of the alkanephosphonic acid or pyroalkanephosphonic acid.

The water formed at these temperatures in a condensation reaction is removed from the reaction vessel by the inert gas stream and can be collected in a cold trap connected in between.

The pyrolysis time is, depending on the alkanephosphonic acid and the temperature set, between 10 and 20 hours.

After the pyrolysis is complete, the anhydride formed can be directly distilled from the reaction vessel (see DE-A 4126235). For this purpose, the passing in of inert gas is stopped and the vacuum and/or the temperature are increased until the alkanephosphonic anhydride distills and is thus isolated in pure form.

The product purity is determined by reacting alkanephosphonic anhydride with water to give the corresponding alkanephosphonic acid. This consumes one mol of water per mol of alkanephosphonic acid. Reaction of a known amount of water with a certain amount of alkanephosphonic anhydride (e.g. one mol) and determination of the residual water content (e.g. by the Karl Fischer method) after the reaction enables the anhydride content in the product to be concluded by comparison of the actual and theoretical water consumptions. $^{31}$P-NMR of the hydrolysate enables a further check as to whether the monomer units in the anhydride are actually made up exclusively of the corresponding alkanephosphonic groups.

Alkanephosphonic anhydrides can be used as condensation aids or as intermediates in the preparation of organophosphorus products. Furthermore, they can be used for preparing agents for flame retardation, for metal extraction or corrosion protection.

The following examples illustrate the invention without limiting it to them.

Comparative example using a method similar to that of DE-A 2811628:

220 g of methanephosphonic acid are placed in an apparatus as described in DE-A 2811628 and heated to from 300° to 320° C. at a pressure of from 0.1 to 0.3 mbar. After only three hours, part of the methanephosphonic anhydride formed begins to distill. Since the elimination of water was not complete at this point in time, water continues to form from the thermal condensation in the bottom of the apparatus and backreacts with the methanephosphonic anhydride distilled off to give pyromethanephosphonic acid. The distillate thus obtained has an anhydride content of only about 60%.

EXAMPLE 1

400 g of methanephosphonic acid are heated to 200° C. under a nitrogen atmosphere in a round-bottom flask fitted with internal thermometer, gas inlet capillary and short distillation bridge. On reaching 200° C., the apparatus is evacuated and nitrogen is subsequently passed through the melt in such a way that a vacuum of 3 mbar is obtained. The temperature is then increased to 290° C. After pyrolysis for 10 hours, the passing in of nitrogen is stopped. The vacuum is thereby improved to 0.5 mbar and at the same time the anhydride formed begins to distill (temperature at top 250° C., bottom temperature 300° C., 0.5 mbar). The methanephosphonic anhydride is collected in the receiver as a colorless melt. It has an anhydride content of 90%. Yield 82%.

EXAMPLE 2

Using a method similar to Example 1, 400 g of pyromethanephosphonic acid are pyrolyzed in 15 hours at 270° C. Distillation at a bottom temperature of 300° C., 0.5 mbar and a temperature at the top of 250° C. gives an 86% yield of the anhydride of methanephosphonic acid having an anhydride content of 92%.

EXAMPLE 3

In a similar apparatus to Example 1, 500 g of propanephosphonic acid are heated to 200° C. in an argon atmosphere and the apparatus is subsequently evacuated. Argon is passed through the melt via an inlet tube fitted with a frit in such a way that a vacuum of 4 mbar is obtained. The temperature is then increased to 270° C. and the melt is pyrolyzed for 18 hours. The anhydride of propanephosphonic acid can subsequently be distilled at a bottom temperature of 270° C. and 2 mbar. This gives an 87% yield of a viscous oil having an anhydride content of 80%.

We claim:

1. A process for preparing alkanephosphonic anhydrides of the formula (I)

where R is straight-chain or branched unsubstituted $C_1$–$C_6$-alkyl and $n \geq 3$, which comprises pyrolytically eliminating water from an alkanephosphonic acid of the formula (II) or a pyroalkanephosphonic acid of the formula (III)

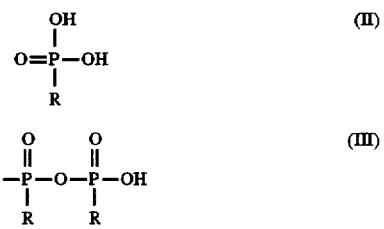

where R is straight-chain or branched $C_1$–$C_6$-alkyl, without addition of solvent and removing the water from the reaction mixture by means of an inert gas stream.

2. The process as claimed in claim 1, wherein R is methyl, ethyl or propyl, and n is from 3 to 150.

3. The process as claimed in claim 1, wherein the pyrolysis is carried out at a temperature between 220° and 350° C.

4. The process as claimed in claim 1, wherein the inert gas stream is passed through the melt during the reaction in such a way that with simultaneous evacuation there is obtained a vacuum of from 2 to 10 mbar.

5. The process as claimed in claim 4, wherein R is methyl and n is from 5 to 100.

6. The process as claimed in claim 5, wherein the pyrolysis is carried out at a temperature between 250° and 350° C.

7. The process as claimed in claim 6, wherein the inert gas stream is passed through the melt during the reaction in such a way that with simultaneous evacuation there is obtained a vacuum of from 3 to 4 mbar.

8. The process as claimed in claim 1, wherein the pyroalkanephosphonic acid of formula (III) is present.

9. The process as claimed in claim 1, wherein said inert gas is nitrogen or argon.

10. The process as claimed in claim 8, wherein the inert gas is nitrogen or argon.

11. The process as claimed in claim 4, wherein the temperature is selected so that in said vacuum the temperature is from 30° to 70° C. below the corresponding boiling or sublimation point of the alkanephosphonic acid or pyroalkanephosphonic acid.

12. The process as claimed in claim 10, wherein the temperature is selected so that in the vacuum the temperature is from 40° to 60° below the corresponding boiling or sublimation point of the alkanephosphonic acid or pyroalkanephosphonic acid.

13. The process as claimed in claim 6, wherein the pyrolysis is carried out from 10 to 20 hours.

14. The process as claimed in claim 12, wherein the pyrolysis is carried out from 10 to 20 hours.

15. The process as claimed in claim 1, wherein the anhydride content is between 80 and 92% of the product produced.

16. The process as claimed in claim 14, wherein the anhydride content is between 80 and 92% of the product produced.

17. The process as claimed in claim 16, wherein R is methyl and n is from 5 to 100.

18. The process as claimed in claim 17, wherein the pyrolysis is carried out at a temperature between 250° and 350° C.

19. The process as claimed in claim 18, wherein the inert gas stream is passed through the melt during the reaction in such a way that with simultaneous evacuation there is obtained a vacuum of from 3 to 4 mbar.

20. The process as claimed in claim 1, wherein said inert gas is nitrogen.

* * * * *